(12) United States Patent
Vaillant

(10) Patent No.: US 10,507,157 B2
(45) Date of Patent: Dec. 17, 2019

(54) INTERFACE FOR CONSTRUCTING TRAJECTORY IN AN ENVIRONMENT AND ENVIRONMENT ASSEMBLY AND TRAJECTORY CONSTUCTION INTERFACE

(71) Applicant: Yannick Vaillant, La Vacherie (FR)

(72) Inventor: Yannick Vaillant, La Vacherie (FR)

( * ) Notice: Subject to any disclaimer, the term of this patent is extended or adjusted under 35 U.S.C. 154(b) by 0 days.

(21) Appl. No.: 15/517,419

(22) PCT Filed: Oct. 1, 2015

(86) PCT No.: PCT/FR2015/052635
§ 371 (c)(1),
(2) Date: Apr. 6, 2017

(87) PCT Pub. No.: WO2016/055721
PCT Pub. Date: Apr. 14, 2016

(65) Prior Publication Data
US 2018/0235833 A1  Aug. 23, 2018

(30) Foreign Application Priority Data
Oct. 7, 2014  (FR) ...................................... 14 59619

(51) Int. Cl.
*G01C 21/36* (2006.01)
*G09B 21/00* (2006.01)
(Continued)

(52) U.S. Cl.
CPC ............ *A61H 3/061* (2013.01); *A61H 9/0078* (2013.01); *G01C 21/20* (2013.01);
(Continued)

(58) Field of Classification Search
CPC ............ G01C 21/3492; G01C 21/3626; G01C 21/3691; G01C 21/20; G01C 21/3652;
(Continued)

(56) References Cited

U.S. PATENT DOCUMENTS

| 5,470,233 A | 11/1995 | Fruchterman et al. |
| 6,486,784 B1 | 11/2002 | Beckers |

(Continued)

FOREIGN PATENT DOCUMENTS

| DE | 10 2011 119 864 | 6/2013 |
| FR | 2 771 626 | 6/1999 |

OTHER PUBLICATIONS

Written Opinion dated May 19, 2016 for International application No. PCT/FR2015/052635 (with English translation).

(Continued)

*Primary Examiner* — Dionne Pendleton
(74) *Attorney, Agent, or Firm* — Fay Sharpe LLP

(57) ABSTRACT

An environment assembly and interface for constructing trajectory (1) in the environment, the trajectory construction interface (1) including a mapping (2a) of the environment, the environment including at least one object, wherein the trajectory construction interface (1) includes: a memory (2) in which is stored the mapping (2a); a system for real-time calculation (6); a system for determining position of a user (3); a system for determining real azimuth of the user (4); a system for indication by haptic stimulation of the position of the at least one object (7), said system for indication of the position of the at least one object (7) being controlled by the system for real-time calculation (6); and a system for indication by haptic stimulation of the actual azimuth of the at least one object (8), said system for indication of the actual azimuth being controlled by the means of real-time calculation (6).

20 Claims, 3 Drawing Sheets

(51) Int. Cl.
  *G06F 3/01* (2006.01)
  *A61H 3/06* (2006.01)
  *G06K 9/00* (2006.01)
  *G06F 1/16* (2006.01)
  *G07C 9/00* (2006.01)
  *G01C 21/20* (2006.01)
  *A61H 9/00* (2006.01)
  *A61F 9/08* (2006.01)
  *A61H 23/02* (2006.01)
  *A61H 15/00* (2006.01)

(52) U.S. Cl.
  CPC ..... *G01C 21/3652* (2013.01); *G01C 21/3664* (2013.01); *G06F 1/163* (2013.01); *G06F 3/016* (2013.01); *G06K 9/00201* (2013.01); *G06K 9/00664* (2013.01); *G07C 9/00126* (2013.01); *G09B 21/003* (2013.01); *A61F 9/08* (2013.01); *A61H 23/0218* (2013.01); *A61H 2003/063* (2013.01); *A61H 2015/0021* (2013.01); *A61H 2201/164* (2013.01); *A61H 2201/1604* (2013.01); *A61H 2201/165* (2013.01); *A61H 2201/1619* (2013.01); *A61H 2201/1635* (2013.01); *A61H 2201/1645* (2013.01); *A61H 2201/5048* (2013.01); *A61H 2201/5064* (2013.01); *A61H 2201/5079* (2013.01); *A61H 2201/5084* (2013.01); *A61H 2201/5092* (2013.01); *A61H 2201/5097* (2013.01); *A61H 2203/0431* (2013.01); *A61H 2205/021* (2013.01)

(58) Field of Classification Search
  CPC ...... G01C 21/3664; G06Q 50/30; G08G 1/07; G08G 1/096811; G08G 1/096844; G08G 1/096855; G08G 1/143; G08G 1/096775; G08G 1/144; G08G 1/166; H04L 67/26; H04W 36/32; H04W 48/04; H04W 84/005; H04N 21/25841; G05D 1/0027; G05D 1/0212; G06F 17/30557; G06F 3/016; G06F 3/017; G06F 3/0481; G07C 9/00158; A61F 9/08; A61H 2003/063; A61H 2015/0021; A61H 2201/1604; A61H 2201/1619; A61H 2201/1635; A61H 2201/164; A61H 2201/1645; A61H 2201/165; A61H 2201/5048; A61H 2201/5064; A61H 2201/5079; A61H 2201/5084; A61H 2201/5092; A61H 2201/5097; A61H 2203/0431; A61H 2205/021; A61H 23/0218; A61H 3/061; A61H 9/0078; G09B 21/003

See application file for complete search history.

(56) References Cited

U.S. PATENT DOCUMENTS

| | | | |
|---|---|---|---|
| 2007/0030363 A1* | 2/2007 | Cheatle | H04N 1/00183 348/239 |
| 2008/0120029 A1 | 5/2008 | Zelek et al. | |
| 2011/0015934 A1* | 1/2011 | Rowe | G06Q 30/02 705/1.1 |
| 2011/0054773 A1 | 3/2011 | Chi et al. | |
| 2011/0251755 A1* | 10/2011 | Widmann | B60R 1/00 701/36 |
| 2011/0268300 A1 | 11/2011 | DeMers et al. | |
| 2012/0176525 A1* | 7/2012 | Garin | G01C 21/20 348/333.02 |
| 2013/0218456 A1 | 8/2013 | Zelek et al. | |
| 2013/0253834 A1* | 9/2013 | Slusar | G01C 21/3608 701/540 |
| 2014/0038137 A1* | 2/2014 | Hill | G06F 3/016 434/62 |
| 2014/0309864 A1* | 10/2014 | Ricci | H04W 4/21 701/36 |
| 2015/0219463 A1* | 8/2015 | Kang | G08G 1/143 701/117 |
| 2017/0011210 A1* | 1/2017 | Cheong | A61B 5/0022 |
| 2017/0154530 A1* | 6/2017 | Irion | G01C 21/3685 |
| 2017/0173457 A1* | 6/2017 | Rihn | G06F 3/011 |

OTHER PUBLICATIONS

International Search Report dated May 19, 2016 for International application No. PCT/FR2015/052635.
Written Opinion dated May 19, 2016 for International application No. PCT/FR2015/052635.
French Search Report completed Jun. 5, 2015 for French Application No. FR 1459619 (with English translation).
International Preliminary Report on Patentability dated Apr. 11, 2017 for International application No. PCT/FR2015/052635 (with English Explanation).

* cited by examiner

INTERFACE FOR CONSTRUCTING TRAJECTORY IN AN ENVIRONMENT AND ENVIRONMENT ASSEMBLY AND TRAJECTORY CONSTUCTION INTERFACE

This application is the U.S. National Phase of PCT International application No. PCT/FR2015/052635 filed Oct. 1, 2015 (10/01/2015), which claims priority from French Application No. 1459619 filed Oct. 7, 2014 (10/07/2014).

FIELD

The present invention relates to the field of the systems allowing to construct a trajectory in the space, and particularly relates to an interface for constructing a trajectory in a environment and to an environment and trajectory construction interface assembly enabling, according to one configuration, a hands-free and eyes-free displacement, allowing a blind or visually impaired person to construct and follow his/her own trajectory in the environment, or any person without any visual impairment to be guided very accurately using neither his/her sight, nor hearing or hands.

BACKGROUND

It is useful to define, for introductory purposes, the notion of trajectory. A trajectory is a sequence of positions described by a moving point. A trajectory can be trivial: sequence of segments connecting navigation points, or complex: combination of curves with variable radii passing through points associated with tangents to the curve. The trajectory described by a person will depend on an objective: for example, the shortest path or the fastest travel time considering lateral or longitudinal adhesion limits, as a function of the speed. A specialist will be capable of extrapolating in real time his/her optimum trajectory as a function of a limited number of information about his/her travel environment, in combination with his/her own situation (speed, orientation . . . ). Then, he/she will be able to make immediate decisions in an autonomous manner, such as pivot, rotate, slow down and accelerate, without any system imposing them to him/her.

The required and sufficient information needed by the specialist are particular points commonly designated "chord points". It is essential for the specialist to know, at any time and simultaneously, the position, the passage direction and the tangent direction of at least one chord point to extrapolate a complex trajectory. For optimization purposes, he/she should also know his/her own speed. The only information of the position of this point is not sufficient to allow the specialist to extrapolate a complex trajectory. For example, if the chord point is a few centimeters from a wall, it is essential that the specialist integrates to pass through this chord point parallel to the wall. The tangent information specific to the chord point is thus essential for our problem. A simple series of passage points, without this tangent information, is unusable for the construction of complex trajectories.

In the particular field of sports, the objective for the athlete consists in arriving at the end of a path in a minimum time, without exiting limits of the environment imposed to him/her (ski slope, lane in athleticism, limit of the road or velodrome in cycling, limit of the road or circuit for automobile or motorbike).

The athlete should find a balance between his/her speed and his/her capacity to maintain or modify his/her travel direction in the environment. In some sports, additional parameters come into play, such as the capacity of the material to accelerate or decelerate as a function of the speed or the curvature radius, for example.

The optimization of these parameters results in the trajectory described by the athlete in his/her travel environment.

The top athlete is the one who excels both in the technique of his/her particular sport (running, moving quickly on skis, managing a deviation in a car, optimizing braking) and the planning of his/her trajectory in the specific environment imposed to him/her for a trial.

Indeed, the intrinsic performance of the athlete resulting from his/her capacities to control the body technique specific to his/her sport is not sufficient: also, his/her capacity to "read" his/her environment in order to predefine his/her own trajectories will make the difference with the other athletes.

Thus, the best athlete will be the one who will use his/her intrinsic capacities at the maximum in the environment, without exiting its limits. This is the whole purpose of the trajectory: it results from a true expertise of the athlete. It is the combination between the capacities of the athlete and the constraints of the travel environment.

This concretely results in reference points followed by the athlete along his/her path. These points can be passage points, chord points, orientation changing points, deceleration points or acceleration points.

Ideally, these points are predetermined by the athlete and his/her concentration is focused on the reference points at a distance from his/her instantaneous situation.

The system of the invention provides the athletes with innovating media in the complex approach of controlling the trajectories.

The system according to the invention can be used both in an educational approach and in an operational situation, as an efficient information support useful for handling the trajectory.

The great particularity of the system according to the invention is that it allows an efficient use both for blind and visually impaired athletes.

Generally, it is difficult for blind or visually impaired persons to move in an unknown environment without any external assistance such as another aid person or a blind stick.

Thus, there are many touch or sound navigation systems which allow blind or visually impaired persons to move in an environment, the blind or visually impaired persons being guided in the environment via touch or sound information.

The US patent application US2011268300 describes a touch guiding system, the system comprising touch stimulators within a headgear which can provide touch stimuli at different locations around the head in order to transfer information to a person, such as a direction or azimuth, the system further comprising magnetic sensors, accelerometers and/or a GPS. However, the system can provide, through touch, only one type of information at the same time to the user, thereby limiting the amount of trajectory information sent to the user. Moreover, this system does not allow to detect objects of the environment which are not in the mapping of the environment.

The US patent application US2008120029 describes a clothing touch navigation system which transfers position information to the user through touch, the system being able to provide the user, via a belt comprising four touch actuators arranged at the four cardinal points, with direction and distance information using a GPS. However, this system cannot provide the user, through touch, with other navigation information such as information of own azimuth of passage gate or information of limit of the travel environment. In addition, this system does not allow to detect objects of the environment which are not in the mapping of the environment. Furthermore, this system having only four touch actuators, the user orientation accuracy is highly limited. Finally, this system does not allow in any case a high speed use or an optimized handling of the trajectories.

The French patent application FR2771626 describes a system allowing the blind or visually impaired persons to be oriented and guided in an unknown environment, the system comprising transmitters arranged on the path and a portable object comprising touch means to inform the user of the direction to follow according to the direction of the orientation reference, the selected destination and the information transmitted from the transmitters. However, this system cannot provide the user, through touch, with other navigation information such as information of own azimuth of passage gate or information of environment limits. Moreover, the exchange of information between the transmitters and the moving object is performed via a wireless communication, thereby imposing in the object worn by the user a wireless communication receiver. This system does not allow in any case a high speed use or an optimized handling of the trajectories.

The US patent application U.S. Pat. No. 5,470,233 A describes a system allowing a blind person to move in an urban environment. This system does not allow in any case a high speed use or an optimized handling of the trajectories.

The German patent application DE 10 2011 119864 A1 describes a navigation apparatus having a touch interface. This system does not allow in any case a high speed use or an optimized handling of the trajectories. Furthermore, it does not allow a hands-free use.

SUMMARY

According to an embodiment, the present invention relates to an interface for constructing a trajectory in an environment for a user, the user having, at a given time, a position and direction on said trajectory, characterized in that the interface comprises:
first means for transmitting information to the user in a sensory manner;
means for recognizing the environment;
means for calculating and memorizing connected to the first and second means for transmitting information to the user in a sensory manner, to the means for recognizing the environment, and to the means for calculating a distance for receiving information therefrom and transmitting instructions thereto;
the means for recognizing the environment allowing to indicate in real time, to the user, information about a direction of a future passage gate on the trajectory via the first means for transmitting information to the user in a sensory manner.

According to a particular embodiment, the interface further comprises:
second means for transmitting information to the user in a sensory manner;
means for calculating a distance;
the means for calculating a distance allowing to indicate in real time, to the user, distance information to said future passage gate on the trajectory via the second means for transmitting information to the user in a sensory manner.

In the present application, the expression "sensory manner" shall be understood to be a haptic, namely touch or sound, manner.

Thus, according to an embodiment, the invention comprises a target passage gate defined by a passage left limit and a passage right limit, its relative direction with respect to the frame of reference specific to the user and its distance with respect to the user. In operation, the target passage gate can be stationary or moving in the environment.

The interface comprises:
a capacity of reading the environment by camera (TV, HD, UHD, 4K, IR);
a system for detecting a distance to a target (radar, radio system, image processing, . . . );
a device for calculating information to be transmitted to the user;
a system for the haptic transmission of information on the right and left limits of the passage gate;
a system of haptic or sound information about the distance between the user and the passage gate.

Thus, according to an example in the field of sports, such as athleticism during a race, a camera is positioned on a blind athlete, for example his/her chest. A non-impaired athlete, the guide of the blind athlete, has a visual marker on his/her back (for example, a cross-type specific pattern or another pattern). During the race, the system continuously detects the position of the guide ahead of the blind athlete. It continuously informs the user of the direction between the axis of the camera and the guide in a haptic manner.

Generally, the camera(s) could also be used for detecting potential anomalies, such as moving or stationary obstacles. This could allow to alert the user.

On the other hand, this system also allows to determine the speed and orientation of the camera, thus of the user, by a scrolling reading of predefined environment markers (known spacing of standard ground markers, for example).

According to a particular embodiment, the interface according to the invention further comprises third means for transmitting information to the user in a sensory manner, the means for recognizing the environment allowing to indicate in real time, to the user, left limit and right limit information of said future passage gate via the third means for transmitting information to the user in a sensory manner.

The limits of the environment are advantageously transmitted to the user according to a time projection, for example at 0, 0.1, 1, or several seconds, according to user situation data.

According to a particular embodiment, the interface according to the invention further comprises means for determining a distance between the user and another reference user situated downstream on the same trajectory.

According to an example, such as a ski slope, one or more cameras are positioned on a blind athlete, for example his/her helmet. A non-impaired skier, the guide of the blind skier, has a visual marker on his/her back (for example, a specific pattern). During the race, the system continuously detects the position of the guide ahead of the blind athlete, as well as his/her distance using a radar system or radio system (radio transmitter on the guide, radio receiver on the blind athlete, with a system for determining a distance to the radio source).

The system continuously informs the user of the direction between the axis of his/her head and the guide in a haptic manner, and the distance between the guide and the user in a haptic manner or audibly.

According to a particular embodiment, the interface according to the invention further comprises an environment relational database, containing the set of components constituting the environment and their respective position and distance relations, and means for localizing the user in the environment.

The environment relational database is a database of environment points associated with coordinates, potentially supplemented with data specific to points or areas of the environment. In more detailed versions, such environment relational database could be found in mapping databases.

The interface could advantageously comprise means for localizing the position of the user and its derivatives (speed, acceleration), such means being a GPS, reference boundaries visible by TV, HD, UHD, 4K or infrared camera, an accelerometer, an inertial navigator, electronic compasses, or a telephone network localization system, etc.

The addition of the mapping and of the means for localizing the position of the user and its derivatives allows an autonomous use of the system, without any guide.

The systems of cameras can allow, on one hand, a redundancy of position information, which is an advantage for the reliability of the information, but also a direct detection of the actual environment, in particular for visual signals in real time: obstacle not mapped, flag indicating a hazardous situation, etc.

According to a particular embodiment, the interface according to the invention further comprises fourth means for transmitting information to the user in a sensory manner for indicating, to the user, the passage direction of said future passage gate.

Thus, according to an example in the field of sports, in athleticism, for a race of 400 m (with lanes), a camera is positioned on a blind athletic user, for example his/her chest. The system is set for indicating the information in real time about the position, the right and left limits and the passage orientation of a moving virtual passage gate permanently arranged at 5 meters (configurable data) ahead of the athletic user.

The camera continuously provides the information to the trajectory construction interface about the delimitation lines of the lane of the athlete (position, bend). The trajectory construction interface calculates in real time the situation of the virtual gate with respect to the athletic user using the data collected by the camera. The trajectory construction interface calculates the passage direction of the gate in real time by using the curvature radius of the lane lines. The trajectory construction interface transmits it in a haptic manner to the user, for example with a system of one or more vibrating cells or with a system of mechanical pointers. The system indicates in real time the position of the user with respect to the right and left limits of the passage gate, thereby allowing the user to continuously position himself/herself in his/her lane.

This system allows, for example, a blind person to participate in races in lanes (100 m, 200 m, 400 m in athleticism, for example) without any guide which is essential at present.

According to a particular embodiment, the interface according to the invention further comprises at least one of fifth means for transmitting information to the user in a sensory manner for indicating, to the user, the position of the reference user, sixth means for transmitting information to the user in a sensory manner for indicating, to the user, the speed of the reference user, and seventh means for transmitting information to the user in a sensory manner for indicating, to the user, the acceleration of the reference user.

The term "speed" refers to a vector value (direction, orientation, magnitude) and not to the simple speed value.

Coupled to the user position and orientation information, this particularly allows to add the reference user orientation information in real time, as well as that of the distance between the reference user and the user, thereby avoiding any radar and/or radio system.

The reference user acts as a moving primary passage gate: here, the available information are the direction of this target, its orientation in real time and its distance, which is useful for an even more effective extrapolation of the trajectory.

According to a particular embodiment, each of the first to seventh means for transmitting information to the user in a sensory manner is one of a haptic tool positioned on a body part of the user and a sound tool.

According to a particular embodiment, each haptic tool is one of:
  one or more pointers in contact with a body part of the user;
  contact wheels, sliding on a slide;
  vibrating cells in contact with a body part of the user, optionally activated by air;
  mini-cylinders operated by one of air, liquid and electromagnetic means in order to contact a body part of the user;
  pressing points operated by inflating pockets;
  compressed air nozzles;
  a system of mechanical fingers controlled by a pneumatic network, preferably without any metal component.

Thus, one or more pointers can move on a slide in a mechanical, electromagnetic, pneumatic or hydraulic manner. The displacement of each pointer is determined according to the evolution of the haptic information to be transmitted. Each pointer can be in contact with the user via a non-abrasive surface, a wheel or a vibrating device.

According to a particular embodiment, each sound tool is at least one of a headset and at least one speaker.

The sound tool can transmit information about the speed of the user and his/her proximity to a point, limit or area of the environment, or alert the user of the proximity of an obstacle. The sound information about the speed could be transmitted to the user in different ways: absolute speed or relative speed with respect to a reference speed at a location where the user is situated, information transmitted by a voice talking to the user, or by frequency modulation. The sound information about the proximity can be transmitted to the user in different ways: countdown before beep, frequency modulation.

The sound tool can separately use the "left" and "right" channels to distribute two different types of information (speed on one hand, proximity on the other hand, for example).

According to a particular embodiment, each haptic tool is positioned on the head, neck, chest, arms and/or legs of the user.

According to a particular embodiment, each means for recognizing the environment is constituted by one of an infrared camera, a TV camera, a photographic sensor connected to an image recognizing computer program. Obviously, it can comprise more than one camera, for example to have a 360° view.

Advantageously, at least two cameras can be used to determine the relative position of a body part with respect to a frame of reference which can be the body itself or the environment of the user.

According to a first example, a camera is attached on the user's head, another on his/her chest. By differential analysis of the images of the two cameras, it is possible to determine the position of the user's head with respect to the chest.

According to another example, a camera is attached on the user's head, and another camera is attached on a car in which the user is situated. By differential analysis of the images of the two cameras, it is possible to determine the position of the user's head with respect to the vehicle.

The stereoscopic vision can also allow the calculation of distance.

According to a particular embodiment, the means for calculating a distance are constituted by at least one of a radar, a radio wave transmitter-receiver pair, an ultrasound wave transmitter-receiver pair.

The system continuously informs the user of the direction between the axis of the camera and the guide in a haptic manner, and the distance between the guide and the user in a haptic manner or audibly.

According to a particular embodiment, the means for determining a distance between the user and a reference user situated downstream on the same trajectory is constituted by a camera system worn by the user, connected to an image recognizing program and a marker adapted to be recognized on the reference user, such that the image processing software, after capturing the image of the marker on the reference user, is able to determine, from the image of the marker, the distance between the user and the reference user.

According to a particular embodiment, the relational database is a mapping of the environment, the means for localizing the user in the environment being constituted by at least one of a GPS system, a Galileo system or a Glonass system.

The present invention relates, according to an embodiment, to an assembly of an environment and a trajectory construction interface in the environment, the trajectory construction interface comprising a mapping of the environment, the environment comprising at least one object, the trajectory construction interface comprising at least one means for real-time calculation, one means for determining the position of a user, one means for determining the actual azimuth of the user, one means for indicating by haptic stimulation the position of the at least one object, and one means for indicating by haptic stimulation the own azimuth of the at least one object. This assembly allows to provide, in a haptic manner, the user, who can be a blind or a visually impaired person, with several navigation information simultaneously, such as direction and azimuth information, such that the user can choose an environment trajectory and move thereon. In addition, this assembly allows to detect objects positioned in the environment, without the latter being in the mapping of the environment, and without the trajectory construction interface having a wireless communication means. Thus, the assembly according to the present invention allows any person to naturally move in his/her environment without using his/her sight, said assembly providing, in real time, the user with the synthesized information of his/her travel environment which will allow him/her to make his/her own movement choices. In the present application, the expression "user actual azimuth" refers to the direction followed by this user, namely the axis of the user's head. For a sighted person, the actual azimuth is the direction of his/her gaze.

The principle of the invention is based on the fact that, during the displacement of the user, the user's body uses the position of the head as a natural frame of reference. The position of the head naturally brings the body on a trajectory in the space, therefore the trajectory construction interface of the invention informs in real time the user of the direction to follow and thus the direction of the objective with respect to the body, specific information allowing to define a trajectory also being sent in real time to the user by haptic and/or sound means.

The present invention thus relates to an assembly of an environment and a trajectory construction interface in the environment, the trajectory construction interface comprising a mapping of the environment, the environment comprising at least one object, characterized in that the trajectory construction interface comprises:

a memory in which the mapping is stored;
means for real-time calculation;
means for determining the position of a user;
  means for determining the actual azimuth of the user;
  means for indicating by haptic stimulation the position of the at least one object, said means for indicating by haptic stimulation the position of the at least one object being controlled by the means for real-time calculation according to the mapping stored in the memory, to user position information from the means for determining the position and/or to user actual azimuth information from the means for determining actual azimuth; and
  means for indicating by haptic stimulation the own azimuth of the at least one object, said means for indicating by haptic stimulation the own azimuth of the at least one object being controlled by the means for real-time calculation according to the mapping stored in the memory, to user position information from the means for determining the position and/or to user actual azimuth information from the means for determining actual azimuth.

The memory can particularly be one of a random access memory, a read-only memory, a volatile memory or a flash memory.

The means for real-time calculation can particularly be one of a microprocessor, a microcontroller, an on-board system, a FPGA or an ASIC.

Thus, position and own azimuth information of at least one object in the environment can be indicated in real time to the user in a haptic manner according to the position and to the actual azimuth of the user, the at least one object in the environment being in the mapping of the environment stored in the memory, the user thus having information about the trajectory to follow in the environment, the user knowing the position of the target object to follow or to cross as well as the travel direction of the target to follow or of the crossing direction of the object to cross.

Thus, the user can do without the sight in order to move in the environment, the information about the trajectory to follow in the environment being transmitted to him/her in a haptic manner.

It can be noted that the trajectory construction interface can be entirely worn by the user, for example when the user walks or goes skiing, or be worn together by the user and a vehicle driven by the user, for example when the user drives a car, a motorbike, etc.

According to a particular feature of the invention, the trajectory construction interface further comprises means for indicating the distance of the at least one object with respect to the user, said means for indicating the distance of the at least one object being controlled by the means for real-time calculation according to the mapping stored in the memory, to user position information from the means for determining position and/or to user actual azimuth information from the means for determining actual azimuth. Indications about the speed and the acceleration of the user can also be transmitted to him/her.

Thus, the user also receives, in real time, indications about the distance of the at least one object in the environment, the user adapting his/her speed and trajectory according to the distance to the object in the environment.

According to a particular feature of the invention, the trajectory construction interface further comprises means for indicating environment limits, said means for indicating environment limits being controlled by the means for real-time calculation according to the mapping stored in the memory, to user position information from the means for determining position and/or to user actual azimuth information from the means for determining actual azimuth.

Thus, the user further receives, in real time, indications about the environment limits, such as indications about a path edge limit, the user knowing the limits of the environment in which he/she moves in order to ensure his/her safety and to know, for example when turning, the travel environment limits not to cross.

According to a particular feature of the invention, the means for determining position is one of a GPS, a Galileo system and a Glonass system, and/or one or more cameras, preferably infrared (IR) cameras, said cameras being adapted to localize objects of the environment, so that the means for real-time calculation can determine the position of the user using the mapping.

Thus, the GPS, Galileo or Glonass system allows to localize in real time the position of the user in the environment, so as to know his/her position with respect to the mapping stored in the memory.

In addition, the one or more cameras allow to localize objects in the environment by detecting, for example, the color or shape of the objects or detecting, for example, the frequency of a signal visible by sensors of cameras (IR or not), so as to localize in real time the position of the user compared to the information contained in the mapping stored in the memory.

In the case of IR cameras, the IR cameras detect IR waves radiated by certain specific objects of the environment.

It can be noted that the means for determining position contain, preferably, a GPS and several cameras for redundancy of position information, the assembly thus being more secured.

According to a particular feature of the invention, the means for determining actual azimuth are an electronic compass or an inertial navigator positioned on the user's head.

Thus, the inertial navigator/electronic compass allows the trajectory construction interface to know in real time the orientation of the user's head, the means for real-time calculation sending the trajectory information to the user according to the orientation of his/her head.

According to a particular feature of the invention, the trajectory construction interface further comprises one or more accelerometers, the one or more accelerometers being included, if appropriate, within the inertial navigator.

Thus, the one or more accelerometers allow the means for real-time calculation to know in real time the acceleration of the user in the environment.

The invention can thus be provided with an electronic compass and accelerometers, or with an inertial navigator or a combination of an inertial navigator, an electronic compass and accelerometers.

According to a particular feature of the invention, the means for indicating by haptic stimulation the position of the at least one object is a haptic tool positioned on a body part of the user, and the means for indicating by haptic stimulation the own azimuth of the at least one object is another haptic tool positioned on a body part of the user.

The expression "own azimuth of an object" refers to the direction and orientation of the object according to its actual frame of reference. Thus, for a gate, the expression "own azimuth" of the gate refers to its direction and orientation with respect to its actual frame of reference. Thus, the haptic tools allow to inform the user respectively of object position information and object own azimuth information without the user needing the sight, the user being for example a blind or visually impaired person.

According to a particular feature of the invention, the means for indicating a distance of the at least one object is a haptic tool positioned on a body part of the user and/or a sound tool.

Thus, the object distance indication information can be provided to the user in a haptic manner and/or audibly, without the user needing the sight.

According to a particular feature of the invention, the means for indicating environment limits is a haptic tool positioned on a body part of the user and/or a sound tool.

Thus, the environment limits indication information can be provided to the user in a haptic manner and/or audibly, without the user needing the sight.

According to a particular feature of the invention, the one or more haptic tools are a headset or one or several speakers.

In the case where the trajectory construction interface is entirely worn by the user, the sound tool can be a headset and, in the case where the trajectory construction interface is worn together by the user and a vehicle, the sound tool can be speakers arranged in the vehicle.

According to a particular feature of the invention, the at least one object is a trajectory primary gate, characterized by a left limit, a right limit and an azimuth, the own azimuth of the primary gate corresponding to the passage direction of the primary gate by the user.

A trajectory gate is a passage gate through which the user should pass when moving on the trajectory in the environment, the passage gate being defined by a left limit and a right limit, and by a passage direction, the passage gate being defined materially in the environment or dynamically by the trajectory construction interface, or set on-the-fly by the user.

The trajectory primary gate is the next passage gate that the user should cross on the trajectory in the environment. Thus, the assembly transmits, to the user, position information of the left and right limits of the primary gate via the means for indicating position of the object, own azimuth information of the primary gate via the means for indicating own azimuth of the object and, optionally, distance information of the left and right limits of the primary gate via the means for indicating distance of the object, the user having all information required to move towards the primary gate and cross it.

According to a particular feature of the invention, the environment further comprises an object of trajectory secondary gate, corresponding to the passage point following the passage point of the primary gate, the secondary gate becoming the new primary gate after the passage of the previous primary gate.

The trajectory secondary gate is the passage gate following the trajectory primary gate, the secondary gate becoming the new primary gate after the passage of the previous primary gate.

Thus, before the passage of the current primary gate, the user can receive position information of the secondary gate via the means for indicating a position of the object, thereby allowing the user to anticipate his/her future trajectory when moving in the environment.

According to a particular feature of the invention, the environment further comprises one or several environment edge objects, preferably a left limit edge and a right limit edge.

Thus, the user can further receive environment limits information via the means for indicating environment limits, the environment edge objects being defined in the mapping of the environment and/or arranged materially in the environment and detected by the cameras.

According to a particular feature of the invention, the environment further comprises one or several reference objects, positioned beforehand on the mapping or on-the-fly in the environment.

These reference objects are markers for specific actions (for example, braking, turning, jump, or environment elements which should be managed in a dynamic manner, such as obstacles (for example, movable or stopped car, moving person, traffic light, or game partners (for example, opponents or teammates in a team sport) or a particular object (for example, ball, the markers for specific actions being previously arranged on the mapping or detected by the cameras, the other environment elements managed in a dynamic manner being detected by the cameras.

Thus, the user can receive information about the reference objects via the different indication means, thereby further improving his/her knowledge of the environment.

According to a particular feature of the invention, each haptic tool is one of:
one or several pointers in contact with a body part of the user;
contact wheels, sliding on a slide;
vibrating cells in contact with a body part of the user, optionally activated by air;
mini-cylinders operated by one of air, liquid and electromagnetic means in order to contact a body part of the user;
pressing points operated by inflating pockets;
compressed air nozzles;
a system of mechanical fingers controlled by pneumatic network, preferably without any metal component.

Thus, one or several pointers can move on a slide in a mechanical, electromagnetic, pneumatic or hydraulic manner. The displacement of each pointer is determined according to the evolution of the haptic information to be transmitted. Each pointer can be in contact with the user via a non-abrasive surface, a wheel or a vibrating device.

The one or more haptic tools used in the scope of the present invention can also be connected objects. In a car, a seat belt provided with haptic information devices can indicate the direction of a primary and/or secondary gate, and/or its distance and/or orientation. The steering wheel of a car or ship, the control column of an aircraft, the handles of a trolley or any device gripped by the user for a displacement can be used as a haptic tool according to its capacities: a setting system will allow to define the exact nature of the information taken in charge by the connected object, as well as their calibration, according to the characteristics of the connected object and the preferences of the user.

Thus, each haptic tool can accurately inform the user of the information of the associated indication means, each haptic tool being arranged on a different body part of the user.

According to a particular feature of the invention, each haptic tool is positioned on the head, neck, chest, arms and/or legs of the user.

Two contact wheels sliding on a slide can, for example, be arranged on the user's head in order to inform the user of position and distance information of the primary gate, the position of both contact wheels with respect to the user's head indicating the position of both limits of the primary gate with respect to the orientation of the user's head, the spacing of both contact wheels informing the user of the distance of the primary gate with respect to the user.

Several vibrating cells can, for example, be arranged at a constant pitch around the user's head in order to inform the user of actual azimuth information of the primary gate, one of the vibrating cells vibrating to indicate the own azimuth of the primary gate with respect to the orientation of the user's head.

Several mini-cylinders operated by electromagnetism, air or liquid can, for example, be arranged at a constant pitch around the user's chest so as to inform the user of position information of the secondary gate, only one mini-cylinder being operated at the same time to indicate the position of the secondary gate with respect to the orientation of the user's head.

Several inflatable pockets can, for example, be arranged on each user's arm so as to inform the user of environment limits information, only one pocket being inflated on each arm to indicate the distances of the left and right limits of the environment, respectively, with respect to the user.

It can be noted that these examples are not limiting and any type of haptic tool can be arranged on any body part of the user, without departing from the scope of the present invention.

According to a particular feature of the invention, the trajectory construction interface is able to be wirelessly connected to environment specific applications such as a guiding system application, the trajectory construction interface receiving in real time information about the environment, such as changes of the environment, from the environment specific applications.

According to an embodiment, the present invention relates to an assembly of an environment and a trajectory construction interface in the environment such as described below, the trajectory construction interface comprising a mapping of the environment, the environment comprising at least one object, characterized in that:
the means for calculating and memorizing store the mapping;
the means for calculation are in real time;
the trajectory construction interface further comprises means for determining the position of a user and means for determining the actual azimuth of the user;
the first means for transmitting information to the user in a sensory manner indicate the direction of the at least one object, said first means for transmitting information to the user in a sensory manner being controlled by the means for real-time calculation according to the mapping stored in the means for calculating and memorizing, to user position information from the means for determining position and/or to user actual azimuth information from the means for determining actual azimuth; and
the second means for transmitting information to the user in a sensory manner indicate the distance of the at least one object, said second means being controlled by the means for real-time calculation according to the mapping stored in the means for calculating and memorizing, to user position information from the means for determining position and/or to user actual azimuth information from the means for determining actual azimuth.

According to a particular embodiment, the means for calculating a distance calculate a distance of the at least one object with respect to the user, said means for calculating a distance of the at least one object being controlled by the means for real-time calculation according to the mapping stored in the means for calculating and memorizing, to user position information from the means for determining position and/or to user actual azimuth information from the means for determining actual azimuth.

According to a particular embodiment, the means for determining position is one of a GPS, a Galileo system, a Glonass system, and at least one camera, preferably an infrared (IR) camera, but also optionally a TV, HD, UHD or 4K camera, the at least one camera being able to localize objects of the environment such that the means for real-time calculation can determine the position of the user using the mapping.

According to a particular embodiment, the means for determining actual azimuth is one of an electronic compass and an inertial navigator positioned on the user's head.

According to a particular embodiment, the trajectory construction interface further comprises at least one accelerometer, the one or more accelerometers being included, if appropriate, within the inertial navigator.

According to a particular embodiment, the at least one object is a trajectory primary gate, characterized by a left limit, a right limit and an own azimuth, the own azimuth of the primary gate corresponding to the passage direction of the primary gate by the user.

According to a particular embodiment, the environment further comprises an object of trajectory secondary gate, corresponding to the passage point following the passage point of the primary gate (34), the secondary gate becoming the new primary gate after the passage of the previous primary gate (34).

According to a particular embodiment, the trajectory construction interface is able to be wirelessly connected to environment specific applications such as a guiding system application, the trajectory construction interface receiving in real time information about the environment, such as changes of the environment, from the environment specific applications.

Thus, for example, in the case where the environment is an airport or a subway, the trajectory construction interface can receive in real time information about the airport or subway via applications specific to the airport or the subway, the information being related, for example, to a departure gate, a luggage retrieval area or a connection guidance in the case of an airport, or a subway terminal or a change guidance in the case of a subway.

According to an embodiment, several trajectory construction interfaces according to the present invention can be interconnected to share data between them. Thus, for example, if only one member of a group provided with an interface according to the invention receives the position information, all the other interfaces of the group benefit from this information. The relative positions of the members of the group are known from each other using the sharing of information and the means for recognizing the environment (cameras). Any individual interface according to the invention can be considered as a primary or secondary gate by another interface according to the invention.

According to a particular embodiment, the interface comprises means for detecting the tilt around the axis y, which is in the horizontal reference plane of the user and perpendicular to the frontal reference axis of the user, coupled to a haptic transmitter device called "vertical system" which informs the user of an angular position around this very same axis y.

The haptic transmitter device is composed of one or several touch pointers which transmit "more tilted upwards" or "more tilted downwards" information to the user according to a setting adjusted by the user according to his/her sensitivity. The means for detecting the tilt can be a wired or wireless connected object, integral with any body part of the user (head, arm, etc.) or with any object used for designating a target (binoculars, lamp, weapon, etc.). The haptic transmitter device related to the information processed by this detection means can be arranged on any body part of the user.

This device allows the ALT-Sen to designate a target not only in the reference plane of the user, but also in the space.

According to a particular embodiment, the trajectory construction interface can comprise a deported system for determining the head position: the head position is determined by an external system, for example one or more cameras attached on a support (handlebars or instrument panel of a vehicle, for example). This system for determining the head position can then complement or substitute the on-board system integral with the user (compass, accelerometer, inertial navigator, angular position detection, etc.).

According to a particular embodiment, the trajectory construction interface can comprise a deported system for determining the gaze direction: the user gaze direction is determined by an external system, for example one or more cameras attached on a support (handlebars or instrument panel of a vehicle, for example). This system for determining the gaze direction can then complement or substitute the on-board system integral with the user (compass, accelerometer, inertial navigator, angular position detection, etc.).

According to a particular embodiment, the trajectory construction interface can comprise a system for indicating obstacles: a system for detecting stationary or moving obstacles (radar, ultrasound detection system, cameras) is coupled to a haptic belt which informs the user in real time of the presence of obstacles. This belt can have one or several haptic information transmission devices. These haptic information transmission devices indicate the proximity of the obstacles by frequency variation as well as, optionally, the relative direction thereof with accuracy depending on the number of haptic information transmission devices of the system for detecting stationary or moving obstacles.

According to a particular embodiment, the trajectory construction interface can comprise a system for indicating non-planned obstacles: a system for detecting stationary or moving obstacles (radar, ultrasound detection system, cameras) is coupled to a sound signal management system. In case of detecting at least one stationary or moving obstacle, the system indicates, via a sound, the presence, distance and direction of the one or more detected obstacles.

According to a particular embodiment, the trajectory construction interface can comprise a video system in front of the user's eyes. This system displays, superimposed on the environment, complementary information for facilitating the displacement of the user. The nature and position of the displayed information depend on the parameters processed by the interface (position of the head or the user, speed, etc.). For example, this video system can allow to display a virtual guide as part of the use by a visually impaired person during speed events (alpine ski, running, cycling), or display information such as the speed or proximity of a particular point, of a limit, in addition to the sound and haptic data, by means of color codes or stroboscopic effects.

According to a particular embodiment, the trajectory construction interface can comprise a radio system for determining the distance to a target. The target is provided with a radio wave transmitting active system. The user is equipped with a reception system which detects the strength of the received signal. The distance to the target is determined by the measure of the received signal, which depends on the distance to the source. There can be one or several targets: the targets are identified by their own signal.

According to a particular embodiment of the invention, a radar worn by the user can be used for detecting the objects in his/her environment.

BRIEF DESCRIPTION OF DRAWINGS

To better illustrate the object of the present invention, preferred embodiments will be described below, for illustrative and non-limiting purposes, in reference to the appended drawings.

In these drawings.

DETAILED DESCRIPTION

Figure 1:
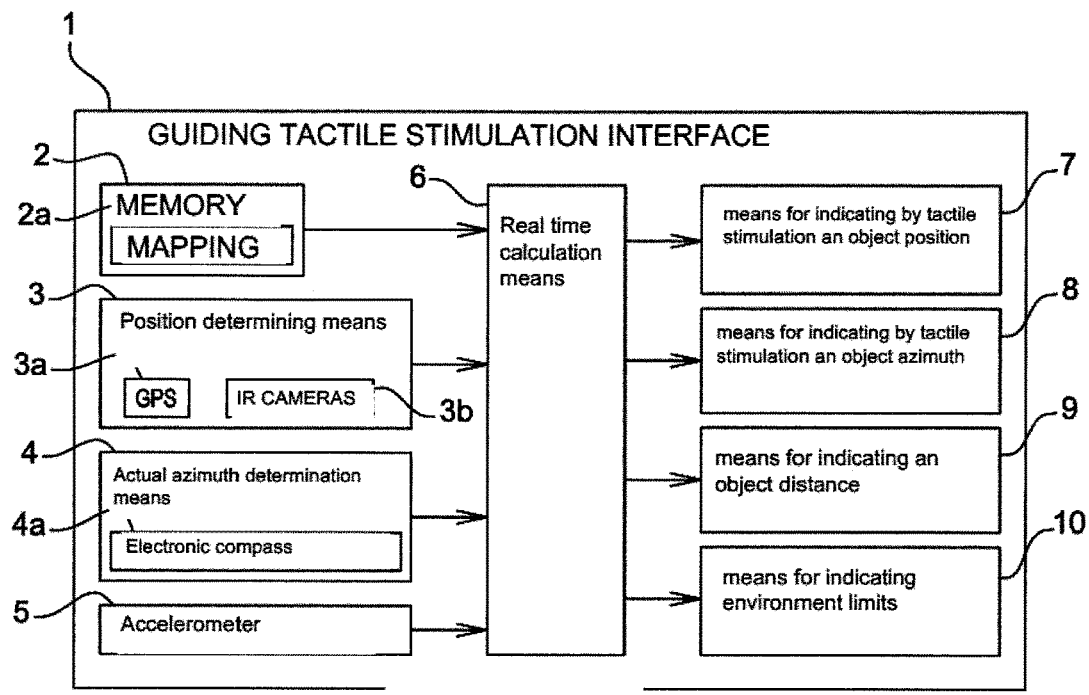
FIG. 1 is a block diagram of a trajectory construction interface according to the present invention.

If referring to FIG. 1, a trajectory construction interface 1 according to the present invention is shown.

An assembly of an environment and a trajectory construction interface comprises a trajectory construction interface 1 and an environment (not shown in FIG. 1), a user of the trajectory construction interface 1 moving on a trajectory in the environment, the environment comprising at least one stationary or moving object in the environment.

The trajectory construction interface 1 comprises a memory 2 in which a mapping 2a of the environment is stored, means for determining a position of the user 3, means for determining azimuth of the user's head 4, and an accelerometer 5. Although it is not described in relation to the figures, said accelerometer can advantageously be replaced with or complemented by an inertial navigator, without departing from the scope of the present invention.

The memory 2 can particularly be one of a random access memory, a read-only memory, a volatile memory or a flash memory.

The means for determining a position of the user 3 comprises a GPS 3a and several IR cameras 3b.

The GPS 3a allows to determine in real time the GPS position and the speed of the user in the environment by defining the three-dimensional position of the user into GPS coordinates, the GPS 3a having high frequencies and with a high accuracy, preferably about 5 cm.

The IR cameras 3b allow to localize IR objects in the environment so as to determine in real time the position of the user with respect to these IR objects, the IR objects being in the mapping 2a or not, the IR objects transmitting intrinsic data to the environment (for example, limits, signs or messages) or anomaly data (for example, static obstacle or moving object).

The GPS 3a and the IR cameras 3b allow to obtain redundancy of user position information, the assembly thus being more secured.

It can be noted that the means for determining a position of the user 3 could have only a GPS 3a or only IR cameras 3b, without departing from the scope of the present invention.

It can be noted that the means for determining a position of the user 3 could also have a Galileo or Glonass system instead of the GPS 3a, without departing from the scope of the present invention.

It can be noted that the cameras could also be non-IR cameras, without departing from the scope of the present invention, the cameras then being adapted to localize shapes or colors of objects of the environment.

The means for determining the actual azimuth of the user 4 comprises an electronic compass 4a, the electronic compass 4a being arranged on the user's head and allowing to measure in real time the absolute orientation of the user's head. Although it is not described in relation to the figures, said electronic compass 4a can advantageously be replaced with or complemented by an inertial navigator, without departing from the scope of the present invention.

The accelerometer 5 allows to measure in real time the three-dimensional and angular accelerations of the user.

It can be noted that the trajectory construction interface 1 may not have an accelerometer 5, without departing from the scope of the present invention.

The trajectory construction interface 1 further comprises means for real-time calculation 6, said means for real-time calculation 6 being connected to the memory 2, the means for determining a position 3, the means for determining actual azimuth 4 and the accelerometer 5 so as to receive their respective measured information.

The means for real-time calculation 6 can be, in particular, one of a microprocessor, a microcontroller, an an-board system, a FPGA or an ASIC.

The means for real-time calculation 6 perform a compilation of information from the memory 2, the means for determining a position 3, the means for determining actual azimuth 4 and the accelerometer 5 so as to determine in real time the current three-dimensional trajectory of the user in the mapping 2a of the environment, by calculating the orientation of the user's head (via the electronic compass 4a), the speed of the user (via the GPS 3a), the absolute position of the user in the environment (via the GPS 3a), the relative position of the user in the environment (via the IR cameras 3b), and the three-dimensional and angular accelerations of the user (via the GPS 3a and the accelerometer 5), the information consistency being controlled with the redundancy of the information sources.

The trajectory construction interface 1 further comprises means for indicating by haptic stimulation an object position 7, means for indicating by haptic stimulation an object own azimuth 8, means for indicating an object distance 9, and means for indicating environment limits 10.

It can be noted that the trajectory construction interface 1 may not have means for indicating an object distance 9 and means for indicating environment limits 10, without departing from the scope of the present invention.

The means for real-time calculation 6, which calculates in real time information of a trajectory to follow by the user, is connected to the means for indicating by haptic stimulation an object position 7, the means for indicating by haptic stimulation an object own azimuth 8, the means for indicating an object distance 9 and the means for indicating environment limits 10, so as to provide them with respective information of a trajectory to follow.

The means for indicating by haptic stimulation an object position 7 is controlled by the means for real-time calculation 6 according to the mapping 2a stored in the memory 2, to user position information from the means for determining a position 3, to user actual azimuth information from the means for determining actual azimuth 4 and/or to acceleration information from the accelerometer 5, the means for indicating by haptic stimulation an object position 7 informing in a haptic manner the user of the position of at least one object in the environment.

The means for indicating by haptic stimulation an object own azimuth 8 is controlled by the means for real-time calculation 6 according to the mapping 2a stored in the memory 2, to user position information from the means for determining a position 3, to user actual azimuth information from the means for determining actual azimuth 4 and/or to acceleration information from the accelerometer 5, the means for indicating by haptic stimulation an object own azimuth 8 informing in a haptic manner the user of the own azimuth of at least one object in the environment.

The means for indicating an object distance 9 is controlled by the means for real-time calculation 6 according to the mapping 2a stored in the memory 2, to user position information from the means for determining a position 3, to user actual azimuth information from the means for determining actual azimuth 4 and/or to acceleration information from the accelerometer 5, the means for indicating an object distance 9 informing in a haptic manner or audibly the user of the distance of at least one object in the environment with respect to the user.

The means for indicating environment limits 10 is controlled by the means for real-time calculation 6 according to the mapping 2a stored in the memory 2, to user position information from the means for determining a position 3, to user actual azimuth information from the means for determining actual azimuth 4 and/or to acceleration information from the accelerometer 5, the means for indicating environment limits 10 informing in a haptic manner or audibly the user of the distance of environment limits with respect to the user.

The means for indicating by haptic stimulation an object position 7 is a haptic tool positioned on a body part of the user and the means for indicating by haptic stimulation an object own azimuth 8 is another haptic tool positioned on a body part of the user.

The means for indicating an object distance 9 is a haptic tool positioned on a body part of the user and/or a sound tool.

The means for indicating environment limits 10 is a haptic tool positioned on a body part of the user and/or a sound tool.

Thus, the user can do without the sight to move in the environment, the information about the trajectory to follow in the environment being transmitted to him/her in a haptic manner or audibly, the user knowing in real time the position of the next object to cross, as well as the passage direction of the next object to cross.

It can be noted that the trajectory construction interface 1 can be entirely worn by the user, for example when the user walks or goes skiing, or be worn together by the user and a vehicle driven by the user, for example when the user drives a car, a motorbike, etc.

An object of the environment to be crossed by the user is a trajectory primary gate, said trajectory primary gate comprising a left limit, a right limit and an own azimuth, the own azimuth of the primary gate corresponding to the passage direction of the primary gate by the user.

Another object of the environment to be crossed subsequently by the user is a trajectory secondary gate, corresponding to the passage point following the passage point of the primary gate, the secondary gate becoming the new primary gate after the passage of the previous primary gate.

Other objects of the environment are environment edges, preferably a left limit edge and a right limit edge.

Other objects of the environment are markers, positioned beforehand on the mapping 2a or on-the-fly in the environment.

Figure 2:
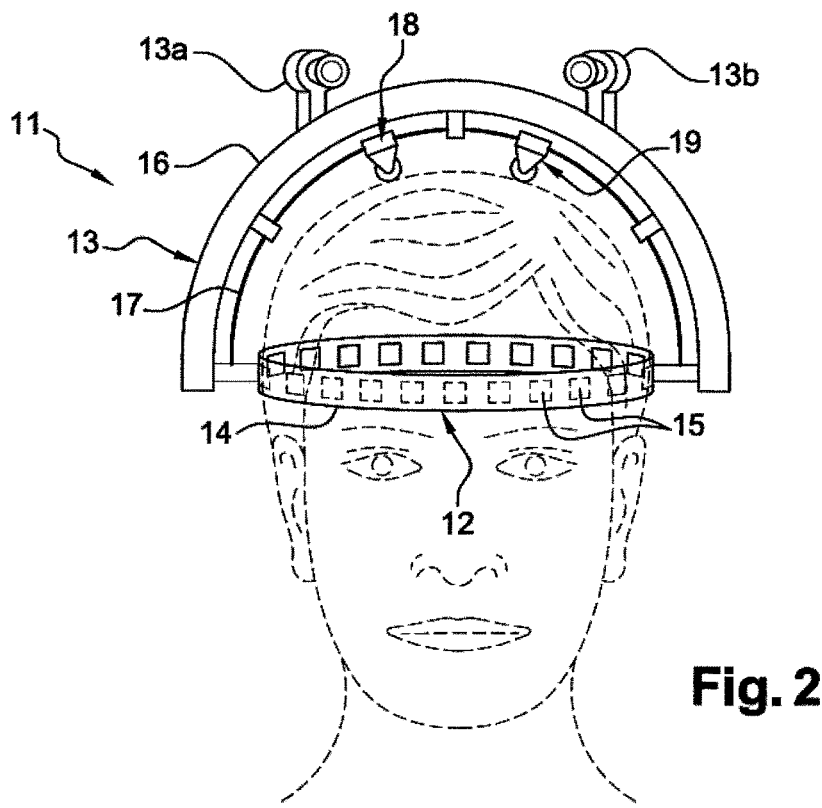
FIG. 2 is a perspective view of a head haptic tool of the trajectory construction interface according to a preferred embodiment of the present invention.
Figure 2A:
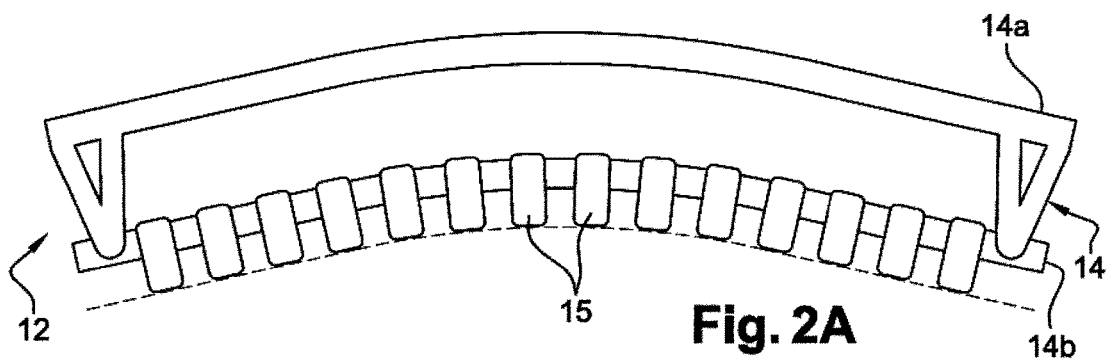
FIG. 2A is a zoom of FIG. 2 on the haptic tool indicating the own azimuth of the primary gate of the head haptic tool.
Figure 2B:
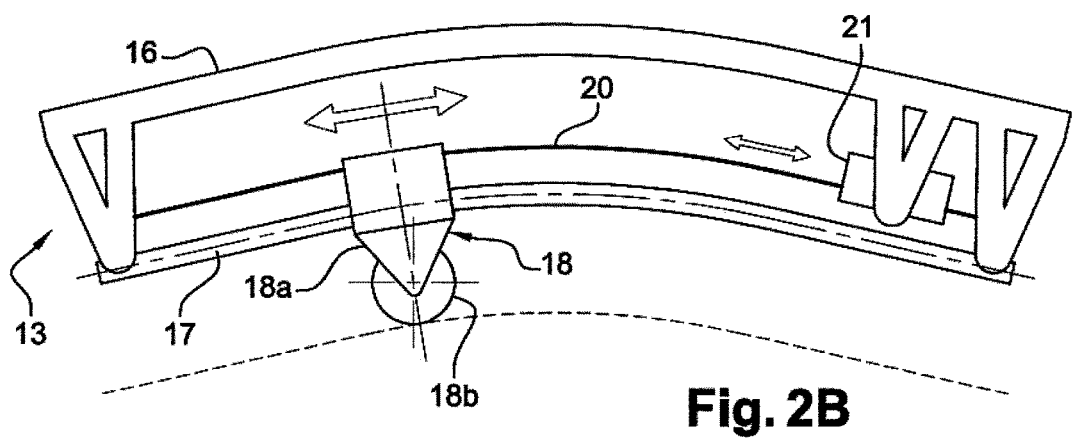
FIG. 2B is a zoom of FIG. 2 on the haptic tool indicating the position of limits of the primary gate of the head haptic tool.

If referring to FIGS. 2, 2A and 2B, a head haptic tool of the trajectory construction interface 1 is shown according to a preferred embodiment of the present invention.

The head haptic tool 11 has a haptic tool indicating primary gate own azimuth 12, a haptic tool indicating primary gate limits positions 13, and two IR cameras 13a, 13b.

The haptic tool indicating primary gate own azimuth has a band 14 arranged around the circumference of the user's head, the band 14 comprising several vibrating cells 15 evenly arranged around the band 14, one of the vibrating cells 15 vibrating in order to inform the user of the own azimuth of the primary gate with respect to the orientation of the user's head.

It can be noted that the haptic tool indicating primary gate own azimuth 12 could also be composed of a haptic pointer array, such as a hood comprising several rows and several columns of vibrating cells, without departing from the scope of the present invention.

The haptic tool indicating primary gate limits positions 13 comprises a rigid gantry 16, arranged on top of the user's head, on which a flexible slide 17 is attached, the gantry 16 being also attached to the band 14 at two opposite sides.

The positions of the left and right limits of the primary gate are respectively defined by moving pointers 18,19 sliding on the slide 17, the pointers 18,19 being always in contact with the user's head.

The IR cameras 13a,13b are attached on top of the gantry 16 and oriented towards the user gaze direction, the IR cameras 13a,13b being intended for detecting IR objects in the environment in order to inform the means for real-time calculation 6.

The gantry 16 can be adjusted for the comfort of the user, and the position of the gantry 16 is adjustable, particularly according to its angular position on the axis passing through the head in a transverse manner (right ear-left ear). The tension of the slide 17 is also adjustable.

The head haptic tool 11 can also be integrated within a helmet which can be attached on the user's head.

If referring more particularly to FIG. 2A, it can be noted that the band 14 has a body support 14a, such as a helmet, on which a semi-rigid support membrane 14b is attached, the membrane 14b carrying thereon the vibrating cells 15 in contact with the user's head, one of the vibrating cells 15 indicating the own azimuth of the primary gate to the user.

If referring more particularly to FIG. 2B, it can be noted that a guide cable 20 is also attached on the gantry 16, parallel to the slide 17.

The moving pointer 18 comprises a frame 18a on which a contact wheel 18b is rotatably attached, the contact wheel 18b being always in contact with the user's head, the frame 18a being fixedly connected to the guide cable 20 and slidably connected to the slide 17.

An electrical motor 21 is also attached on the gantry 16, said electrical motor 21 allowing to move the guide cable 20 parallel to the slide 17, thereby allowing to move the moving pointer 18 on the slide 17 so as to inform the user of a contact point relative to the position of one of the primary gate limits with respect to the user's head.

It can be noted that the electrical motor 21 associated with the moving pointer 18 could also be integral with the frame 18a of the moving pointer 18, or connected to the frame 18a by a belt or chain transmission system, without departing from the scope of the present invention.

It can be noted that the haptic tool indicating primary gate limits positions 13 also comprises an additional guide cable and an additional electrical motor (but not shown) associated with the moving pointer 19 to move the latter on the slide 17 so as to inform the user of a contact point relative to the position of the other of the primary gate limits with respect to the user's head.

The spacing between the two movable pointers 18,19 also informs the user of the distance separating him/her from the primary gate, the two pointers 18,19 drawing closer to each other indicating to the user that the primary gate moves away from the user, and the two pointers 18,19 moving away from each other indicating to the user that the primary gate is getting closer to the user.

It can be noted that the haptic tool indicating primary gate limits positions 13 could also be a system of guided movable crowns (in rotation) comprising each a haptic pointer, without departing from the scope of the present invention.

The part of the moving pointer 18,19 which contacts the user should not be impaired or blocked by the user's hair. For this reason, this contact could be made:
- by a contact wheel 18b which will roll on the user contact surface;
- by a membrane in contact with the user on which the pointer 18,19 will exert a pressure;
- in any case, the pointer 18,19 will be mounted on an adjustable (spring-loaded, pneumatic, hydraulic, etc.) damping system so as to ensure a permanent and convenient contact pressure for the user.

This suspension could also be ensured by the connection between the slide 17 and the device attached on the user's body (for example, helmet).

It can be noted that the haptic tools 12 and 13 could also be arranged on other parts of the user's body, such as the neck, chest, arms and/or legs, without departing from the scope of the present invention.

It can be noted that the haptic tools 12 and 13 could also be composed of a haptic pointer array, such as a hood comprising several rows and several columns of vibrating cells in the case where the tools are arranged on the user's head, without departing from the scope of the present invention.

It can be noted that the haptic tool 12 could also be a pointer in contact with a body part of the user sliding on a slide, mini-cylinders operated by electromagnetism, air or liquid, to contact a body part of the user, or a pressure point operated by inflating pockets, without departing from the scope of the present invention.

It can be noted that the haptic tool 13 could also be vibrating cells in contact with a body part of the user, mini-cylinders operated by electromagnetism, air or liquid to contact a body part of the user, or pressure points operated by inflating pockets, without departing from the scope of the present invention.

Figure 3:
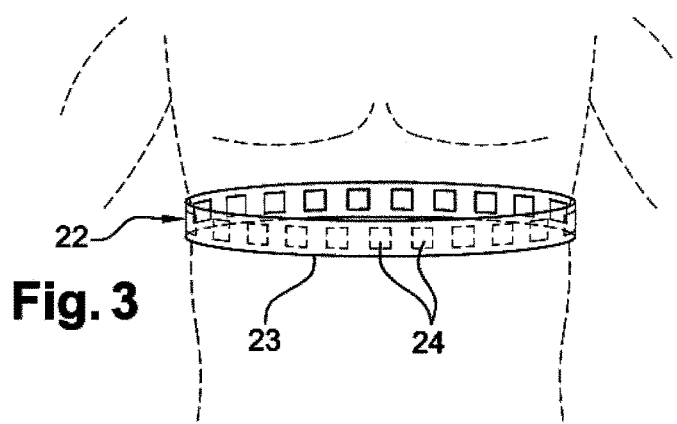
FIG. 3 is a perspective view of a chest haptic tool of the trajectory construction interface according to a preferred embodiment of the present invention.

If referring to FIG. 3, a chest haptic tool 22 of the trajectory construction interface 1 is shown according to the preferred embodiment of the present invention.

The chest haptic tool 22 is a haptic tool indicating a secondary gate position.

The chest haptic tool 22 has a band 23 which is arranged around the circumference of the user's chest, the band 23 comprising several vibrating cells 24 evenly arranged around the band 23, one of the vibrating cells 24 vibrating so as to inform the user of the position of the secondary gate with respect to the orientation of the user's head.

The chest haptic tool 22 can also be attached to a body support such as a belt or a chest protector.

The position of the secondary gate could also be indicated with a type of haptic tool different from that indicating the own azimuth of the primary gate, in order to allow the user to distinguish the information more easily, without departing from the scope of the present invention.

Thus, the chest haptic tool 22 could also be a pointer in contact with the user's chest sliding on a slide, mini-cylinders operated by electromagnetism, air or liquid to contact the user's chest, or a pressure point operated by inflating pockets, without departing from the scope of the present invention.

In addition, the position of the secondary gate could be indicated by a haptic tool on a body part other than the chest, without departing from the scope of the present invention.

In the case where the position of the secondary gate and the own azimuth of the primary gate are both indicated by a haptic tool with vibrating cells, the types of information can be distinguished either by the size of the vibrating contact surface (vibrating plate with larger surface or vibrating segment) or the vibration frequencies.

Figure 4:
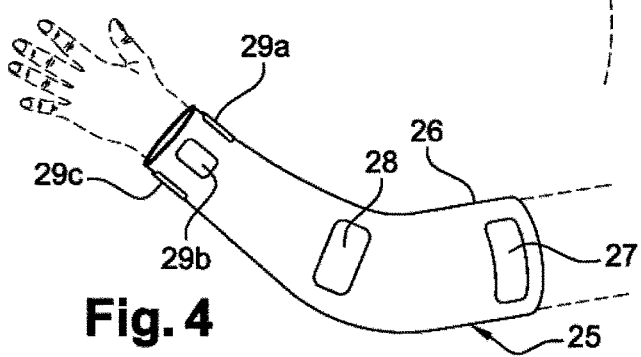
FIG. 4 is a perspective view of an arm haptic tool of the trajectory construction interface according to a preferred embodiment of the present invention.
Figure 4A:
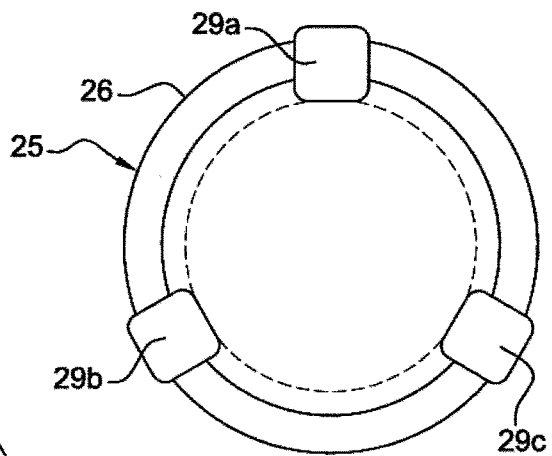
FIG. 4A is a cross-sectional view of the arm haptic tool of FIG. 4 at the wrist.

If referring to FIG. 4 and FIG. 4A, an arm haptic tool of the trajectory construction interface 1 is shown according to the preferred embodiment of the present invention.

The arm haptic tool 25 is a haptic tool indicating environment edge right limit distance, the arm haptic tool 25 being arranged on the user's right arm.

It can be noted that an arm haptic tool, identical but symmetric, is also arranged on the user's left arm as a haptic tool indicating environment edge left limit distance.

The arm haptic tool 25 has a frame 26 adapted to the morphology of the user's arm, such as a semi-rigid support membrane, on which vibrating cells 27,28,29a,29b,29c are attached.

The vibrating cell 27 is arranged at the upper part of the user's arm, the vibrating cell 28 is arranged at the middle of the user's arm, and the vibrating cells 29a,29b,29c are arranged around the user's wrist at equal distance.

One of the vibrating cells 27,28,29a,29b,29c is caused to vibrate so as to indicate in real time the position of the user with respect to the environment edge right limit.

The vibration of the vibrating cell 27 indicates that the user is situated at the center of the environment width, the vibration of the vibrating cell 28 indicates that the user is closer to the right limit than the left limit, and the vibration of one of the vibrating cells 29a,29b,29c indicates that the user is close to the right limit.

The vibrating cells 29a,29b,29c accurately indicate the proximity of the right limit, the vibration of the vibrating cell 29a indicating that the user is close to the right limit, the vibration of the vibrating cell 29b indicating that the user is almost on the right limit, and the vibration of the vibrating cell 29c indicating that the user is situated on the right limit.

It can be noted that the accuracy of the environment edge limit distance information depends on the number of vibrating cells.

It can be noted that the precision of the environment edge limit distance information could be set, the distance between the indicated position and the actual limit being particularly settable, without departing from the scope of the present invention.

It can be noted that the arm haptic tool 25 could also be pointers in contact with the user's arm sliding on a slide, mini-cylinders operated by electromagnetism, air or liquid to contact the user's arm, or a pressure point operated by inflating pockets, without departing from the scope of the present invention.

In addition, the positions of the right and left environment edge limits could be indicated by a haptic tool on a body part other than the arms, without departing from the scope of the present invention.

It can be noted that front and rear environment edge limits could also be indicated to the user according to the same principle with vibrating cells arranged at the front and the rear of a chest protector, for example, without departing from the scope of the present invention.

Figure 5:
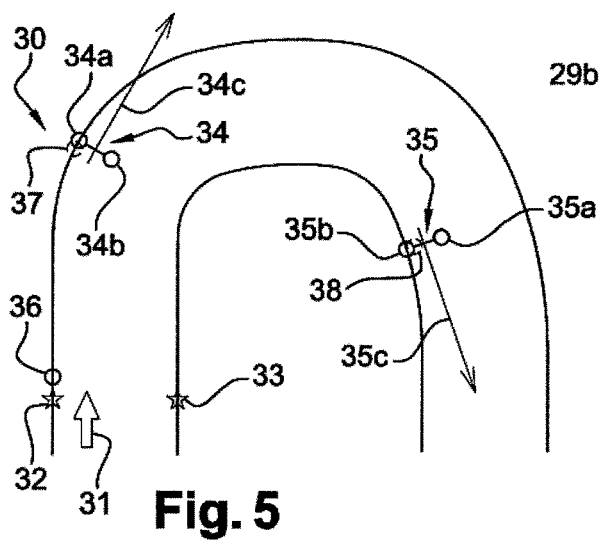
FIG. 5 is a schematic view of an exemplary trajectory in the environment, according to the present invention.

If referring to FIG. 5, a trajectory in the environment is shown as an example according to the present invention.

The environment is a driving path 30 on which the user moves, for example, within a car 31, the driving path 30 comprising a left travel environment limits 32 and a right travel environment limits 33 that the user should not cross, the driving path 30 being, in this example, a hairpin bend.

An object of current primary gate 34 and an object of current secondary gate 35 are on the driving path 30, the user having to successively cross the primary gate 34 and the secondary gate 35 so as to perform the hairpin bend, the primary gate 34 being characterized by a left limit 34a, a right limit 34b and an own azimuth 34c, the secondary gate being characterized by a left limit 35a, a right limit 35b and an own azimuth 35c so as to indicate this information to the user when the secondary gate 35 becomes the new primary gate as soon as the user crosses the current primary gate 34.

The objects of primary gate 34 and secondary gate 35 are in the mapping of the environment and/or arranged materially on the driving path 30 and adapted to be localized by the cameras.

The environment also comprises an object of braking point marker 36, an object of steering point marker 37 and an object of chord point marker 38, the object of braking point marker 36 being arranged at the beginning of the bend, the object of steering point marker 37 being arranged at the primary gate 34, the object of chord point marker 38 being arranged at the secondary gate 35.

The marker objects or objets of reference 36,37,38 are in the mapping and/or materially on the driving path 30 and adapted to be localized by the cameras.

The head haptic tool 11 informs the user of the positions of the left and right limits 34a,34b of the primary gate 34 and the own azimuth 34c of the primary gate 34.

The chest haptic tool 22 informs the user of the position of the secondary gate 35.

Two arm haptic tools 25 inform the user of the left travel environment limits 32 and of the right travel environment limits 33, respectively.

A sound tool informs the user of the crossing of the marker objects 36,37,38 so as to assist the user when driving the car 31 by informing him/her of essential information when passing the bend, namely the braking point, the steering point and the chord point.

The sound tool can be a headset or speakers arranged within the car.

Figure 6:
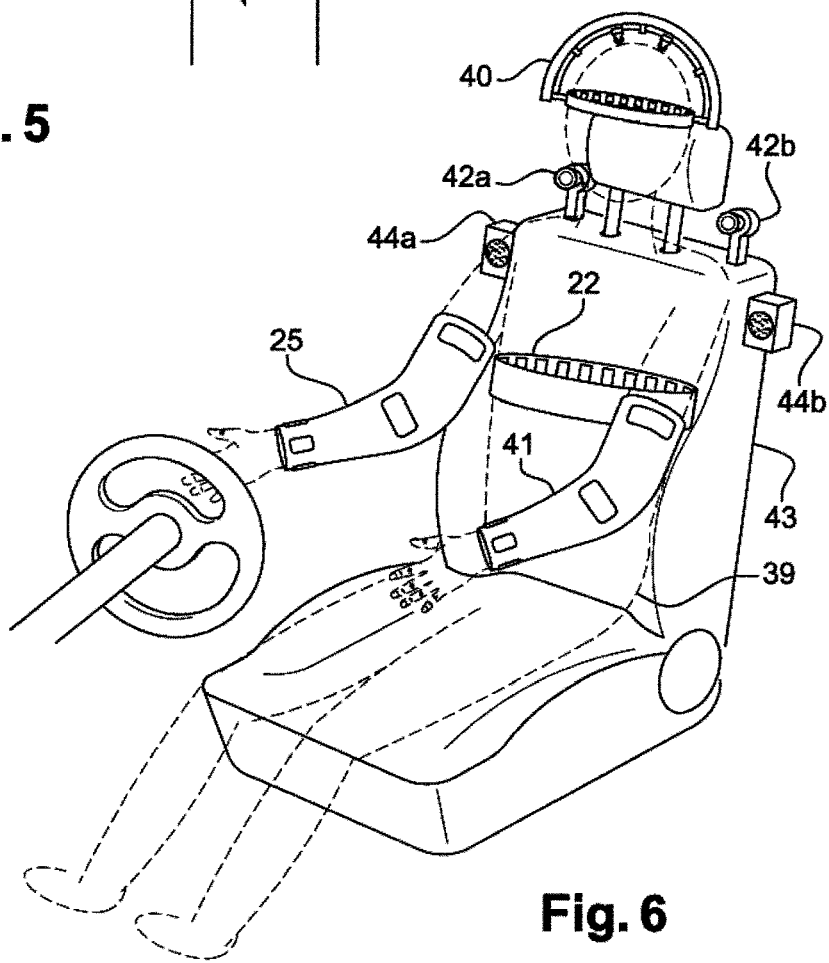
FIG. 6 is a perspective view of a user in a vehicle provided with the trajectory construction interface according to a second preferred embodiment of the present invention.

If referring to FIG. 6, a user 39 is shown within a vehicle provided with the trajectory construction interface 1 according to a second preferred embodiment of the present invention.

The user 39 is installed within a vehicle provided with the trajectory construction interface 1, the user being able to drive the vehicle.

The user 39 carries a head haptic tool 40 identical to the head haptic tool 11, except that it has no IR cameras and has an electronic compass 4a and an accelerometer 5 attached thereon, the electronic compass 4a and the accelerometer 5 being combined with or included into an inertial navigator, the chest haptic tool 22, the arm haptic tool 25, and an arm haptic tool 41 identical to the arm haptic tool 25, except that it indicates the environment edge left limit.

The vehicle is provided with two IR cameras 42a,42b arranged on top of the driver's seat 43 of the vehicle, and two speakers 44a,44b respectively arranged on either side of the driver's seat 43 of the vehicle, the IR cameras 42a,42b being adapted to localize marker objects in the environment, and the speakers 44a,44b being adapted to inform the user audibly of the information of the marker objects.

It can be noted that, as in the first embodiment, the IR cameras could be arranged on a helmet worn by the user, without departing from the scope of the present invention.

The speakers 44a,44b could also indicate the speed of the user by adjusting the sound frequency, the sound volume or "pings" every X meters, or by announcing the achievement of certain predefined speeds, without departing from the scope of the present invention.

The trajectory construction interface 1 continuously records the set of received and played data such that the user can analyze his/her session, this record also serving as a "black box" in case of incident.

Considering the nature of the use of the assembly, it is essential to continuously ensure that the latter is in a good operational state. The different subsystems will be controlled by cross-matching the data of the mapping—cameras—inertial navigator/accelerometers—GPS.

The good mechanical operation will also be controlled, in particular the good position of the pointers.

In case of inconsistency of the information or malfunction of one of the subsystems, the assembly generates alerts until, optionally, switching off.

The assembly can also alert the user if his/her travel exits a predefined frame (for example, the trajectory with respect to the speed).

The autonomy of the trajectory construction interface 1 is ensured by batteries, which are optionally rechargeable by means of photovoltaic cells.

The means for real-time calculation 6 are connected to the different peripherals of the interface (cameras, inertial navigator/compass, haptic tools, etc.) either by electrical cable beam or wirelessly (Bluetooth, Wifi, etc.).

The trajectory construction interface 1 is adapted to be wirelessly connected to environment specific applications, such as a guiding system application, the trajectory construction interface 1 receiving in real time information about the environment, such as changes of the environment, from the environment specific applications.

Non-Limiting Examples of Practical Applications

Navigation Systems

The user can direct his/her gaze towards the correct direction, the motorway exit, the desired street. This use requires only a partial use of the overall capacities of the assembly (only the orientation of the head towards a 2D environment point).

In this case, the trajectory construction interface is controlled by a navigation system. The interface directs in real time the user's head towards the next exit or the next change of direction, or towards the lane in which to drive.

The trajectory construction interface can particularly allow to continue to reliably guide the user in areas which are not covered by a satellite positioning system (such as underground tunnels, for example).

Material:
  a headband on the head connected to the navigation system (in a wired or wireless manner), self-powered;
  a system for indicating a simple direction: crown or slide with a pointer, vibrating system with a limited number of cells (5-10 maximum);
  a compass attached to the headband, or a system of cameras with on-board markers (dots on the instrument panel if this is a car, for example) and/or an accelerometer to localize the line of sight of the head;
  the displacement direction of the GPS system will determine the body direction.

Military Operations for Ground Troops

Accurate designation in real time of the direction of a visual object without any audio or visual contact between the pointer and the user.
  the use of the azimuth to designate the subjective direction of a particular point (injured soldier to be rescued, target, path passage points, etc.);
  the use of the deviation from the primary gate limits for the distance;
    the use of a haptic pointer on the head to raise/lower the head;
      material: compass/accelerometer/level (and/or inertial navigator) (for ground floor/head angle).

Travel by Walking, Skiing, Cycling, Driving, Etc., in a Mapped Environment
  Ski: Downhill or Giant Slalom
  primary gate: right and left limits+own azimuth;
  secondary gate: direction;
  right and left travel limits;
  particular points: chord, bumps, jumps, ice, etc.
  material: cameras with markers, for example, on poles, compass, optionally accelerometer.
  Athleticism: Running in Lanes
  primary gate: right and left limits+own azimuth;
  travel left limit;
  particular points: finish line, relay markers, approaching relay runner, hurdles, etc.
  material: compass, body direction=movement direction.
  Vehicle on Circuit
  primary gate: right and left limits+own azimuth;
  secondary gate: direction;
  left and right travel limits;
  particular points: braking points, steering points, chord points;
  material: compass, body direction=vehicle direction.
  Vehicle in Traffic
  Identical to vehicle on circuit+management of the variable elements of the environment.
  Two-Wheeled Vehicles on Track
  primary gate: right and left limits+own azimuth;
  secondary gate: direction;
  left and right travel limits;
  particular points: braking points, steering points, chord points;
  material: compass, body direction=vehicle direction.
  Team Sports (for Example, Basketball)
  designation of the ball: primary gate+height (distance optionally specified by means of a sound indicator);
  designation of the basket: direction and distance, and then direction and height when close;
  designation of the left-right and front-rear limits (in real time according to the position of the body);
  designation of the direct teammates;
  designation of the direct opponents.

Hands-Free Guidance in any Environment (Such as subway, store, warehouse, hotel, airport, etc.)

Athleticism, Running with a Guide, on a Circuit or not

A reference user (guide) is associated with the user. The reference user constitutes a moving primary gate.

The information transmitted by the means for transmitting information to the user in a sensory manner are: the user-primary gate direction, the right and left limits of the primary gate, the user-primary gate distance, and alerts about the environment.

The means for recognizing the environment are constituted by a camera, for example an infrared camera.

The user-primary gate distance is calculated by reading, via the camera, a marker worn by the reference user or a ground reference. The distance calculation can, in this example, be improved by a radio or radar distance calculation system.

An environment relational database can be used, which comprises a mapping of the environment, with the race lanes, the ground markers, thereby allowing to calculate a speed and/or a user-reference user distance.

The relational database is integrated or accessed by a wireless network, in a conventional manner.

The distances calculated according to the markers are calculated, also in a conventional manner, by image processing.

Athleticism, Running in Lanes without Guide

In this case, the primary gate is a virtual moving primary gate.

The information transmitted by the means for transmitting information to the user in a sensory manner are: the user-primary gate direction, the right and left limits of the primary gate, the own azimuth of the primary gate (defined by calculation according to the ground indications), and alerts about the environment.

The means for recognizing the environment are constituted by a camera, for example an infrared camera.

An environment relational database can be used, which comprises a mapping of the environment, with the race lanes, the ground markers, thereby allowing to calculate a speed and/or a user-primary gate distance.

The relational database is integrated or accessed by a wireless system, in a conventional manner. The distances calculated according to the markers are calculated, also in a conventional manner, by image processing.

Downhill Ski with Guide

As for athleticism with guide, a reference user (guide) is associated with the user. The reference user constitutes a movable primary gate.

The information transmitted by the means for transmitting information to the user in a sensory manner are: the user-primary gate direction, the right and left limits of the primary gate, the own azimuth of the primary gate, the user-primary gate distance, and alerts about the environment.

The means for recognizing the environment are constituted by a camera, for example an infrared camera.

The reference user is provided with means for determining his/her displacement direction, for example an electronic compass.

The distances are calculated by radio or radar means.

In this example, the relational database is not essential.

Downhill Ski with Guide

As for the preceding case, a reference user (guide) is associated with the user. The reference user constitutes a moving primary gate.

The information transmitted by the means for transmitting information to the user in a sensory manner are: the user-primary gate direction, the right and left limits of the primary gate, the own azimuth of the primary gate, the user-primary gate distance, and alerts about the environment.

The means for recognizing the environment are constituted by a camera, for example an infrared camera.

The reference user is, in this example, provided with a GPS/telephone network localization means for localizing him/her, or with a system based on a reading by cameras of environment visual markers, the environment relational database being, in this case, necessary, which comprises the environment visual markers as well as their position.

The distances can, in this example, be calculated by radio and/or radar means.

Downhill Ski without Guide

The primary gate is a virtual stationary or moving gate, calculated by the system. It is not necessary, in this configuration, to have a reference user (guide).

The information transmitted by the means for transmitting information to the user in a sensory manner are: the user-primary gate direction, the right and left limits of the primary gate, the own azimuth of the primary gate, alerts about the environment, and the speed of the user.

The means for recognizing the environment are constituted by one or more camera, for example an infrared type camera.

An environment relational database can be used, which comprises a mapping of the environment.

The relational database is integrated or accessed by a wireless network, in a conventional manner. The distances calculated based on the markers are calculated, also in a conventional manner, by image processing.

The user is provided with a GPS/accelerometer/inertial navigator assembly allowing, in relation to the relational database, to determine his/her position, speed, acceleration and azimuth.

In all these examples, the interface according to the invention allows the user to construct his/her trajectory in the environment. The indicated examples are not limiting, and the one skilled in the art can adapt the interface, based on the examples mentioned above with the indicated interface configurations, adapt the interface to other activities, namely road or circuit cycling, any circuit motorized activity, racing, obstacle running, swimming, running, or even a pedestrian activity in general.

The invention claimed is:

1. An interface for constructing a trajectory in an environment for a user, the user having, at a given time, a position and direction on the trajectory, wherein the interface comprises:
    first haptic means for transmitting information to the user;
    at least one camera connected to an image recognizing computer program for recognizing the environment;
    means for real-time calculation and a memory connected to the first haptic means for transmitting information to the user, and connected to the at least one camera for receiving information therefrom and transmitting instructions thereto;
    the at least one camera allowing to indicate in real time, to the user, information about a direction of a future passage gate on the trajectory via the first haptic means for transmitting information to the user;
    second haptic means for transmitting information to the user;
    means for calculating a distance;
    the means for calculating a distance being connected to the means for real-time calculation and memory and allowing to indicate in real time, to the user, distance information to the future passage gate on the trajectory via the second haptic means for transmitting information to the user;
    the trajectory construction interface further comprising an environment, the trajectory construction interface comprising a mapping of the environment, the environment comprising at least one object, wherein:
    the means for real time calculation and memory store the mapping;
    the trajectory construction interface further comprises means for determining the position of a user and means for determining the actual azimuth of the user;
    the first haptic means for transmitting information to the user indicate the direction of the at least one object, the first haptic means for transmitting information to the user being controlled by the means for real-time calculation according to the mapping stored in the memory, to user position information from the means for determining position and/or to user actual azimuth information from the means for determining actual azimuth; and
    the second haptic means for transmitting information to the user indicate the distance of the at least one object, the second haptic means being controlled by the means for real-time calculation according to the mapping stored in the memory, to user position information from the means for determining position and/or to user actual azimuth information from the means for determining actual azimuth.

2. The trajectory construction interface according to claim 1, further comprising third haptic means for transmitting information to the user, the at least one camera allowing to indicate in real time, to the user, left limit and right limit information of the future passage gate via the third haptic means.

3. The trajectory construction interface according to claim 2, further comprising fourth haptic means for transmitting information to the user for indicating, to the user, the passage direction of the future passage gate.

4. The trajectory construction interface according to claim 3, further comprising at least one of fifth haptic means for transmitting information to the user for indicating, to the user, the position of thea reference user, sixth haptic means for transmitting information to the user for indicating, to the user, the speed of the reference user, and seventh haptic means for transmitting information to the for indicating, to the user, the acceleration of the reference user.

5. The trajectory construction interface according to claim 1, further comprising means for determining a distance between the user and another reference user situated downstream on the same trajectory.

6. The trajectory construction interface according to claim 1, further comprising an environment relational database, containing the set of components constituting the environment and their respective position and distance relations, and means for localizing the user in the environment.

7. The trajectory construction interface according to claim 6, wherein the relational database is a mapping of the environment, the means for localizing the user in his/her environment being constituted by at least one of a GPS, a Galileo or a Glonass system.

8. The trajectory construction interface according to claim 1, wherein:
the first haptic means for transmitting information to the user is one of a haptic tool positioned on a body part of the user and a sound tool; and,
the second haptic means for transmitting information to the user is one of a haptic tool positioned on a body part of the user and a sound tool.

9. The trajectory construction interface according to claim 8, wherein each haptic tool is one of:
one or more pointers in contact with a body part of the user;
contact wheels, sliding on a slide;
vibrating cells in contact with a body part of the user;
mini-cylinders operated by one of air, liquid or electromagnetic means in order to contact a body part of the user;
pressing points operated by inflating pockets;
compressed air nozzles;
a system of mechanical fingers controlled by a pneumatic network.

10. The trajectory construction interface according to claim 8, wherein each sound tool is at least one of a headset and at least one speaker.

11. The trajectory construction interface according to claim 8, wherein each haptic tool is adapted to be positioned on the head, neck, chest, arms and/or legs of the user.

12. The trajectory construction interface according to claim 1, wherein the at least one camera is one of an infrared camera, a TV camera, a photographic sensor connected to an image recognizing computer program.

13. The trajectory construction interface according to claim 1, wherein the means for calculating a distance comprise at least one of a radar, a radio wave transmitter-receiver pair, an ultrasound wave transmitter-receiver pair.

14. The trajectory construction interface according to claim 1, wherein the means for calculating a distance calculate a distance of the at least one object with respect to the user, the means for calculating a distance of the at least one object being controlled by the means for real-time calculation according to the mapping stored in the memory, to user position information from the means for determining position and/or to user actual azimuth information from the means for determining actual azimuth.

15. The trajectory construction interface according to claim 1, wherein the means for determining position is one of a GPS, a Galileo system, a Glonass system and at least one camera, the at least one camera being adapted to localize objects of the environment such that the means for real-time calculation can determine the position of the user using the mapping.

16. The trajectory construction interface according to claim 1, wherein the means for determining actual azimuth are one of an electronic compass and an inertial navigator positioned on the user's head.

17. The trajectory construction interface according to claim 1, wherein the trajectory construction interface is able to be wirelessly connected to environment specific applications such as a guiding system application, the trajectory construction interface receiving in real time information about the environment, such as changes of the environment, from the environment specific applications.

18. An interface for constructing a trajectory in an environment for a user, the user having, at a given time, a position and direction on the trajectory, wherein the interface comprises:
first haptic means for transmitting information to the user;
at least one camera connected to an image recognizing computer program for recognizing the environment;
means for real-time calculation and a memory connected to the first haptic means for transmitting information to the user, and connected to the at least one camera for receiving information therefrom and transmitting instructions thereto;
the at least one camera allowing to indicate in real time, to the user, information about a direction of a future passage gate on the trajectory via the first haptic means for transmitting information to the user;
means for determining a distance between the user and another reference user situated downstream on the same trajectory;
wherein the means for determining a distance between the user and another reference user situated downstream on the same trajectory comprises a camera system worn by the user, connected to an image recognizing program and a marker adapted to be recognized on the reference user, such that the image processing software, after capturing the image of the marker on the reference user, is able to determine, from the image of the marker, the distance between the user and the reference user.

19. The trajectory construction interface in an environment according to claim 18, further comprising:
second haptic means for transmitting information to the user;
means for calculating a distance;
the means for calculating a distance being connected to the means for real-time calculation and memory and allowing to indicate in real time, to the user, distance information to the future passage gate on the trajectory via the second haptic means for transmitting information to the user.

20. An interface for constructing a trajectory in an environment for a user, the user having, at a given time, a position and direction on the trajectory, wherein the interface comprises:
first haptic means for transmitting information to the user;
second haptic means for transmitting information to the user;

at least one camera connected to an image recognizing computer program for recognizing the environment;

means for real-time calculation and a memory connected to the first haptic means for transmitting information to the user, and connected to the at least one camera for receiving information therefrom and transmitting instructions thereto;

the at least one camera allowing to indicate in real time, to the user, information about a direction of a future passage gate on the trajectory via the first haptic means for transmitting information to the user;

said interface further comprising an environment, the trajectory construction interface comprising a mapping of the environment, the environment comprising at least one object, wherein:

the means for real time calculation and memory store the mapping;

the trajectory construction interface further comprises means for determining the position of a user and means for determining the actual azimuth of the user;

the first haptic means for transmitting information to the user indicate the direction of the at least one object, the first haptic means for transmitting information to the user being controlled by the means for real-time calculation according to the mapping stored in the memory, to user position information from the means for determining position and/or to user actual azimuth information from the means for determining actual azimuth; and the second haptic means for transmitting information to the user indicate the distance of the at least one object, the second haptic means being controlled by the means for real-time calculation according to the mapping stored in the memory, to user position information from the means for determining position and/or to user actual azimuth information from the means for determining actual azimuth.

* * * * *

UNITED STATES PATENT AND TRADEMARK OFFICE
CERTIFICATE OF CORRECTION

PATENT NO. : 10,507,157 B2
APPLICATION NO. : 15/517419
DATED : December 17, 2019
INVENTOR(S) : Yannick Vaillant Page 1 of 1

It is certified that error appears in the above-identified patent and that said Letters Patent is hereby corrected as shown below:

On the Title Page

At Item (54) and in the Specification at Column 1, Lines 1-4. The title should read as:
-- INTERFACE FOR CONSTRUCTING TRAJECTORY IN AN ENVIRONMENT AND
ENVIRONMENT ASSEMBLY AND TRAJECTORY CONSTRUCTION INTERFACE --

Signed and Sealed this
Third Day of March, 2020

Andrei Iancu
*Director of the United States Patent and Trademark Office*